(12) United States Patent
Adebiyi et al.

(10) Patent No.: US 11,499,953 B2
(45) Date of Patent: Nov. 15, 2022

(54) FEATURE TUNING—APPLICATION DEPENDENT FEATURE TYPE SELECTION FOR IMPROVED CLASSIFICATION ACCURACY

(71) Applicant: International Business Machines Corporation, Armonk, NY (US)

(72) Inventors: Aminat Adebiyi, San Jose, CA (US);
Mohammed Abdi, San Jose, CA (US);
Andrea Fasoli, San Jose, CA (US);
Alberto Mannari, San Jose, CA (US);
Luisa Bozano, Los Gatos, CA (US)

(73) Assignee: International Business Machines Corporation, Armonk, NY (US)

( * ) Notice: Subject to any disclaimer, the term of this patent is extended or adjusted under 35 U.S.C. 154(b) by 512 days.

(21) Appl. No.: 16/707,805

(22) Filed: Dec. 9, 2019

(65) Prior Publication Data

US 2021/0172919 A1    Jun. 10, 2021

(51) Int. Cl.
*G06N 20/00* (2019.01)
*G01N 33/00* (2006.01)

(52) U.S. Cl.
CPC ..... *G01N 33/0034* (2013.01); *G01N 33/0047* (2013.01); *G06N 20/00* (2019.01)

(58) Field of Classification Search
CPC . G01N 33/0034; G01N 33/0047; G06N 20/00
See application file for complete search history.

(56) References Cited

U.S. PATENT DOCUMENTS

| | | | |
|---|---|---|---|
| 5,299,118 A | 3/1994 | Martens et al. | |
| 7,477,993 B2 | 1/2009 | Sunshine et al. | |
| 9,554,738 B1* | 1/2017 | Gulati | A61B 5/1455 |
| 9,939,412 B2* | 4/2018 | Ichimura | G01N 29/4418 |
| 2003/0068097 A1 | 4/2003 | Wilson et al. | |
| 2005/0216426 A1 | 9/2005 | Weston et al. | |

(Continued)

FOREIGN PATENT DOCUMENTS

| | | |
|---|---|---|
| CN | 102512158 A | 6/2012 |
| CN | 103942526 A | 7/2014 |
| CN | 108052980 A | 5/2018 |

OTHER PUBLICATIONS

Abe et al., Classifier-independent feature selection on the basis of divergence criterion, Pattern Analytical Application 9:127-137 (2006).

(Continued)

*Primary Examiner* — David P Porta
*Assistant Examiner* — Fani Polyzos Boosalis
(74) *Attorney, Agent, or Firm* — Karen Canaan; CanaanLaw, P.C.

(57) ABSTRACT

Provided is a method and system for extracting features from raw data for machine learning processing. Using an array of gas sensors, raw data for at least one compound of interest are extracted based upon the type of output signals. Where the output signals are amplitude-variant, mean features are extracted by chunking the raw data into slices and calculating the mean area under the curve. Where the output signals are amplitude-and-time-variant, mean-plus-slope features are extracted by taking logarithmic values of the raw data and calculating the mean area under the curve.

29 Claims, 10 Drawing Sheets

(56) References Cited

U.S. PATENT DOCUMENTS

| | | | |
|---|---|---|---|
| 2005/0244978 A1* | 11/2005 | Uluyol | G01N 33/0034 422/83 |
| 2011/0008212 A1 | 1/2011 | Ichimura | |
| 2017/0293606 A1 | 10/2017 | Xu et al. | |
| 2019/0101501 A1 | 4/2019 | Sahu et al. | |
| 2019/0111569 A1 | 4/2019 | Chang et al. | |
| 2019/0117964 A1 | 4/2019 | Bahrami et al. | |

OTHER PUBLICATIONS

Adebiyi et al., Rapid strain differentiation of *E. coli*-inoculated Urine using Olfactory-based Smart Sensors, 5th International Conference on Sensors Engineering and Electronics Instrumentation Advances (SEIA' 2019) (2019).

Agrawal et al., Intelligent Software Defined Atmospheric Effect Processing for 5th Generation (5G) Millimeter Wave (MMWave) Communication System, I.J. Wireless and Microwave Technologies 2:15-26 (2018).

Andrew et al., Multi-Stage Feature Selection Based Intelligent Classifier for Classification of Incipient Stage Fire in Building, Sensors 16:1-15 (2016).

Bahraminejad et al., Real-Time Gas Identification by Analyzing the Transient Response of Capillary-Attached Conductive Gas Sensor, Sensors 10:5359-5377 (2010).

Blum et al., Selection of Relevant Features and Examples in Machine Learning, Artificial Intelligence 97:245-271 (1997).

Choi et al., The Wireless Electronic Noses and Mobile Devices Interoperation Based on Internet of Things Technology, Advanced Science and Technology Letters 120:149-152 (2015).

Gardner et al., Enhancing electronic nose performance by sensor selection using a new integer-based genetic algorithm approach, Sensors and Actuators B 106:114-121 (2005).

Gardner et al., Evaluating the Fairness of Predictive Student Models Through Slicing Analysis, International Learning Analytics & Knowledge Conference (LAK19) (2019).

Hall, Correlation-based Feature Selection for Machine Learning, Thesis for Department of Computer Science, The University of Waikato, Hamilton, New Zealand (1999).

Kumar et al., A Novel Method for Evaluation of Band Width of MEMS-Based Embedded Gas Sensor, American Journal of Materials Science 2(4):99-104 (2012).

Leidinger et al., Selective detection of hazardous VOCs for indoor air quality applications using a virtual gas sensor array, Journal of Sensors and Sensor Systems 3:253-263 (2014).

Muller et al., Limitations of High Dimension, Low Sample Size Principal Components for Gaussian Data, Journal of American Statistical Association (JASA) (2008).

Olfert et al., Acoustic method for measuring the sound speed of gases over small path lengths, Review of Scientific Instruments 78:05901.1-05902.8 (2007).

Wang et al., Metal Oxide Gas Sensors: Sensitivity and Influencing Factors, Sensors10:2088-2106 (2010).

Xiaobo et al., Vinegar Classification Based on Feature Extraction and Selection From Tin Oxide Gas Sensor Array Data, Sensors 3:101-109 (2003).

Yu et al., Feature Selection for High-Dimensional Data: A Fast Correlation-Based Filter Solution, Proceedings of the Twentieth International Conference on Machine Learning (ICML-2003) (2003).

* cited by examiner

FEATURE TUNING—APPLICATION DEPENDENT FEATURE TYPE SELECTION FOR IMPROVED CLASSIFICATION ACCURACY

The following disclosure is submitted under 35 U.S.C. 102(b) (1) (A): ADEBIYI et al., Rapid strain differentiation of *E. coli*-inoculated Urine using Olfactory-based Smart Sensors, 5th International Conference on Sensors Engineering and Electronics Instrumentation Advances (SEIA' 2019), 25-27 Sep. 2019.

TECHNICAL FIELD

This invention relates generally to data analytics processing and more specifically, to methods and systems for tuning features from raw data to enable more effective classification accuracy in the pre-processing phase of machine learning data analytics.

BACKGROUND OF THE INVENTION

With machine learning, the extraction of pertinent information and/or features from raw data in the pre-processing phase is critical in order to avoid exhausting the computational power and memory of a computer system. For efficiency, feature types should be chosen that capture information in such a way that the extracted attributes retain as much original information as possible in a compressed manner. The feature types should also highlight the best features from the raw data. Depending on the application of the computer system, the type of features extracted should improve the orthogonality and separation of classes from within the data. Currently, there is no clear system of machine learning for achieving the extraction of the best type of features from raw data and for tuning those best features to a given application.

SUMMARY OF THE INVENTION

The present invention overcomes the need in the art by providing a system for choosing feature types best suited for a given application.

In one aspect, there is provided a method comprising the steps of: (a) obtaining at least one compound of interest for testing on at least one gas sensor; (b) obtaining multiple output signals from the at least one gas sensor for the at least one compound of interest; (c) determining whether each of the multiple output signals is an amplitude-variant signal or an amplitude-and-time-variant signal; (d) for any amplitude-variant output signal, extracting its mean features, and for any amplitude-and-time-variant output signal, extracting its mean-plus-slope features, wherein, mean feature extraction is performed on any amplitude-variant output signals by chunking each of the amplitude-variant output signals into slices and calculating mean area under the curve, wherein values for all of the slices represent the curve for the amplitude-variant output signals, and mean-plus-slope feature extraction is performed on any amplitude-and-time-variant output signals by taking logarithmic values for each of the amplitude-and-time-variant output signals and calculating mean area under the curve, wherein all of the logarithmic values represent the curve for the amplitude-and-time-variant output signals.

In another aspect, there is provided a method for fine-tuning features from raw data comprising: (a) obtaining multiple output signals for at least one compound of interest; (b) determining if the multiple output signals are amplitude-variant or amplitude-and-time-variant through visualization of the output signals; and (c) extracting features from the raw data for the multiple output signals, wherein, mean features are extracted on the raw data from output signals that are amplitude-variant by chunking the raw data into slices and calculating mean area under the curve, wherein values for all of the slices represent the curve for the amplitude-variant output signals, and mean-plus-slope features are extracted on the raw data from output signals that are amplitude-and-time-variant by taking logarithmic values of the raw data and calculating mean area under the curve, wherein all of the logarithmic values represent the curve for the amplitude-and-time-variant output signals.

In one embodiment, there is provided a system comprising: a sensor array comprising a plurality of gas sensors for testing at least one compound of interest, wherein output signals from each sensor of the sensor array are amplitude-variant output signals and/or amplitude-and-time-variant output signals; and a microprocessor comprising at least one algorithm in communication with the sensor array, wherein the microprocessor applies mean feature extraction on any amplitude-variant output signals and mean-plus-slope feature extraction on any amplitude-and-time-variant output signals.

In another embodiment, there is provided a system comprising: a sensor array comprising a plurality of gas sensors for testing at least one compound of interest, wherein output signals from each sensor of the sensor array are amplitude-variant output signals; and a microprocessor comprising at least one algorithm in communication with the sensor array, wherein the microprocessor applies mean feature extraction on the output signals.

In a further embodiment, the microprocessor extracts mean features from the output signals by chunking values of the amplitude-variant output signals into slices and calculating mean area under the curve, wherein values for all of the slices represent the curve for the amplitude-variant output signals.

In another embodiment, there is provided a system comprising: a sensor array comprising a plurality of gas sensors for testing at least one compound of interest, wherein output signals from each sensor of the sensor array are amplitude-and-time-variant output signals; and a microprocessor comprising at least one algorithm in communication with the sensor array, wherein the microprocessor applies mean-plus-slope feature extraction on the output signals.

In a further embodiment, the microprocessor extracts mean-plus-slope features from the output signals by taking logarithmic values for the amplitude-and-time-variant output signals and calculating mean area under the curve, wherein all of the logarithmic values represent the curve for the amplitude-and-time-variant output signals.

In another aspect and embodiment, the extracted mean features and/or the extracted mean-plus-slope features are combined to classify the at least one compound of interest.

In a further aspect and embodiment, the at least one gas sensor is part of a gas sensor array.

In another aspect and embodiment, the output signals are obtained from a gas sensor array.

In a further aspect and embodiment, the compound of interest is a volatile organic compound (VOC).

In another aspect and embodiment, the at least one compound of interest comprises at least two compounds of interest and the amplitude-variant output signals indicate that the at least two compounds of interest share similar functional groups and emit volatiles with similar chemical groups.

In a further aspect and embodiment, the at least one compound of interest is at least two compounds of interest and the amplitude-and-time-variant output signals indicate that the at least two compounds of interest have different functional groups and emit volatiles with different chemical groups.

In another aspect and embodiment, the extracted features are formatted for machine learning processing.

In a further aspect and embodiment, the at least one algorithm formats the extracted features for machine learning processing.

Additional aspects and embodiments of the invention will be provided, without limitation, in the detailed description of the invention that is set forth below.

DETAILED DESCRIPTION OF THE INVENTION

Figure 1:
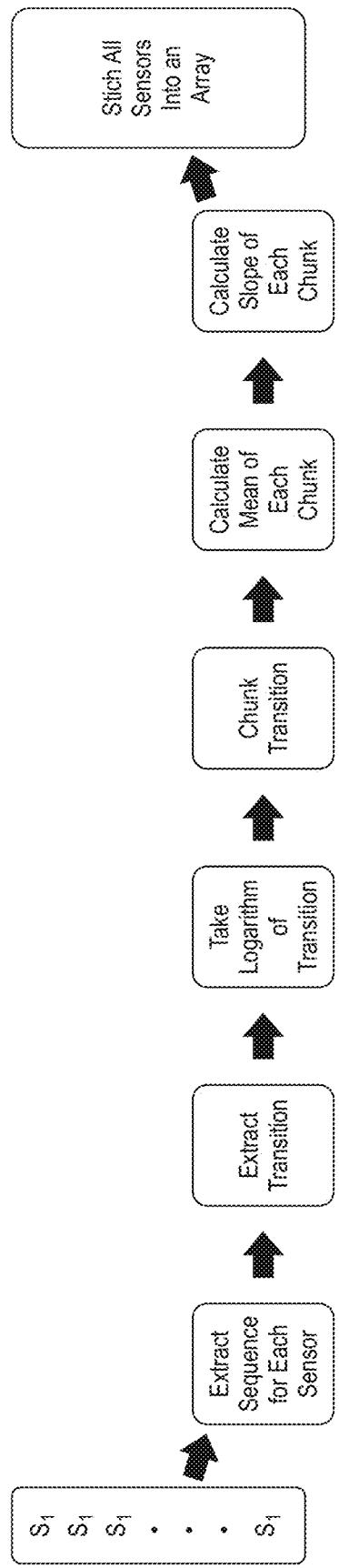
FIG. 1 is a schematic showing the pre-processing steps for an array of gas sensors.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

The term "electronic nose" refers to the use of gas sensor arrays and pattern recognition systems to identify the specific components of an odor and analyze its chemical makeup to identify the odor.

As used herein, the term "area under the curve" or "AUC" is used in its known sense to refer to the area between the graph of y=f(x) and the x-axis. The AUC is calculated with the definite integral formula: $y = \int_a^b f(x^2)dx$. For example, the area under the curve $y = x + 3x^2 dx$ between $x=-2$ and $x=2$ is calculated using the formula $y = \int_{-2}^{2} (x^2+4) dx$ to reach an AUC value of $$y = \left[\frac{x^3}{3} + 4x\right]_{-2}^{2} \text{ or } y = \left[\frac{8}{3} + 8\right] - \left[\frac{-8}{3} + 8\right]$$

for a final AUC value of 5.33. It is to be understood that where the AUC involves logarithmic values, the AUC calculation may also require the derivative (dy/dx) of the curve. Within the context of the present invention, the AUC calculation will generally be carried out with a computer function.

As used herein, the term "mean area under the curve" or "mean AUC" refers to the average AUC calculated across an entire data set (as plotted on a graph). Within the context of the present invention, the data set will be the values of each of the amplitude-variant output signals in a data set and/or the values of each of the amplitude-and-time-variant output signals in a data set.

As used herein, the terms "amplitude-variant" and "amplitude-and-time-variant" refer to the characteristics of gas sensor output signals. As is known to those of skill in the art, gas sensors detect the presence or concentration of gases by producing a potential difference when a material inside the sensor comes in contact with a gas. The potential difference is measured as output voltage resistance against time. A gas sensor shows selectivity between different gases by having different resistance (amplitude) or frequency (time) responses. The response time for a gas sensor is generally defined as the time required for the output signal to achieve a certain percentage of its steady-state value. Within the context of the present invention, amplitude-variant output signals refer to gas sensor output signals that have differing amplitude values, but reach steady-state at approximately the same time. For example, a gas sensor array with six different gas sensors testing for carbon monoxide (CO) and carbon dioxide ($CO_2$) may have individual sensors recording different resistance values for the two gases, but with response times being consistent in all six sensors for both gases (e.g., ~30 sec). Amplitude-and-time-variant output signals refer to gas sensor output signals that have differing amplitude values and that also reach steady-state at different times. For example, a gas sensor array with six different gas sensors testing for nitrogen oxide (NO) and ammonia ($NH_3$) gases may have individual sensors recording different resistance values and frequency response times in all six sensors for the two gases (e.g., 10 sec for $NO_2$ versus 120 sec for $NH_3$).

Data analytics processing generally includes two steps: pre-processing and machine learning. Pre-processing involves chunking, feature extraction, and stitching; and machine learning involves training, weighting, and deployment. Meaningful predictions can only be achieved through accurate feature extraction. FIG. 1 shows an exemplary pre-processing sequence for extracting information from an array of gas sensors, which includes: (i) extracting a sequence for each sensor; (ii) extracting the transition; (iii) taking the logarithm of the transition; (iv) chunking the transition; (v) calculating the mean of each chunk; (vi) calculating the slope of each chunk; and (vii) stitching the inputs from all of the sensors into an array to obtain a final input set for machine learning. Within the context of a gas sensor array, mean features capture the sensitivity and amplitude differences in samples while slope features capture sensor response speed and the recovery and/or shape of sample signals.

The feature extraction methods and systems described herein enhance and tune the pre-processing step of data analytics by identifying attributes of waveforms for different applications in order to improve computational efficiency and classifier accuracy of devices controlled through machine learning algorithms.

Figure 2:
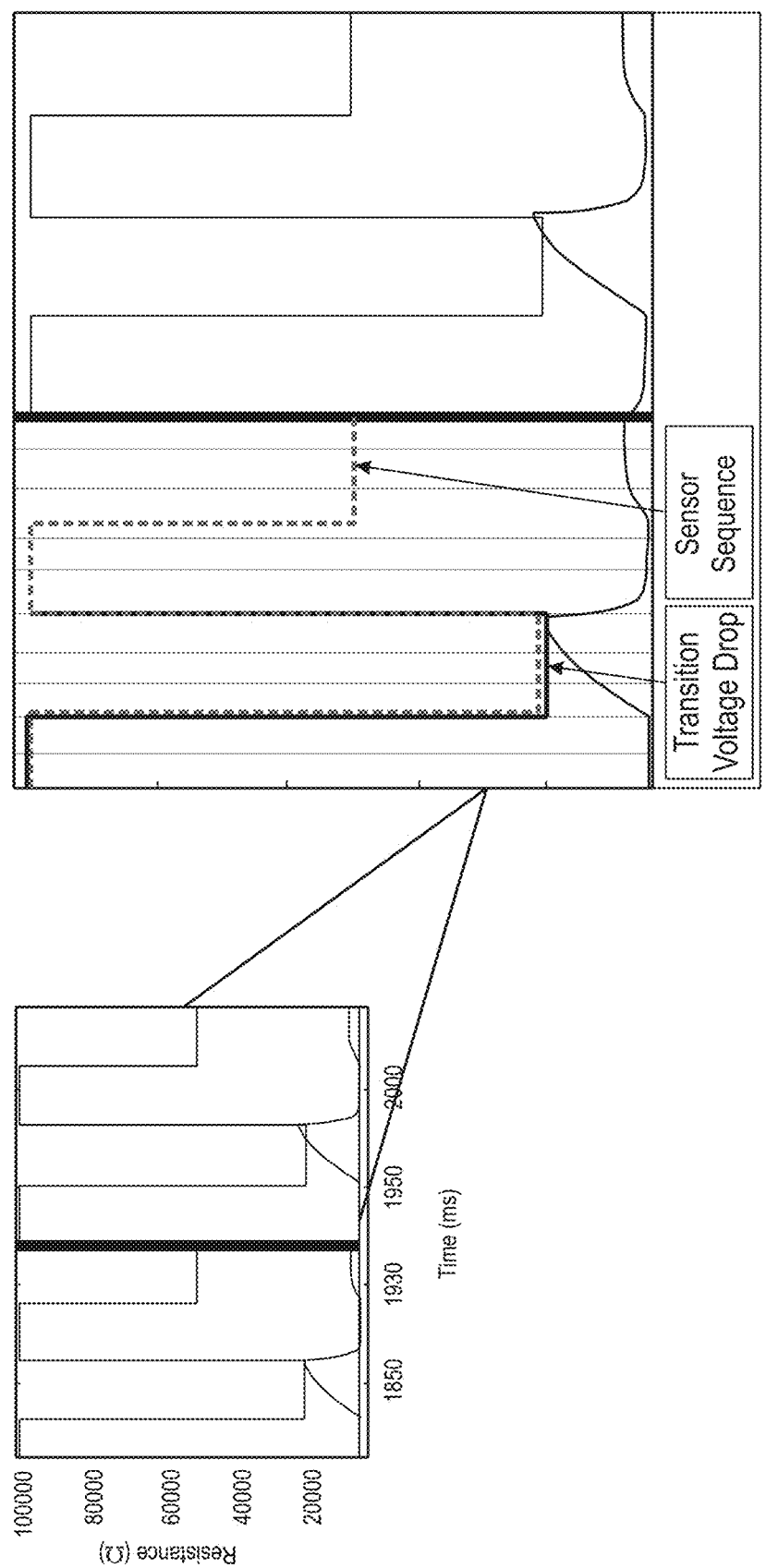
FIG. 2 is a bar graph showing a sensor sequence (dotted lines) and transition (bold lines) for a VOC (vinegar) sample.

FIG. 2 illustrates how feature extraction is applied to sensor resistance output for a vinegar VOC sample. Within the context of a given sensor, a sequence is one full cycle of voltage drops and gains (in order to achieve temperature oscillation) and a transition corresponds to the combination of a single voltage drop and its subsequent gain. In FIG. 2, the sensor sequence (dotted lines) for the vinegar VOC sample is shown as a combination of transition voltage drops (bold lines). The feature extraction involves calculating the mean-plus-slope of a chunk (vertical lines). The five chunks per transition shown therein preserve the resistive changes of the sensor with time. The tunability of a sensor to a target application can thus be highlighted via the attributes of a raw signal. Customized waveforms can further maximize meaningful information throughput compared to transient operation.

Figure 3A:
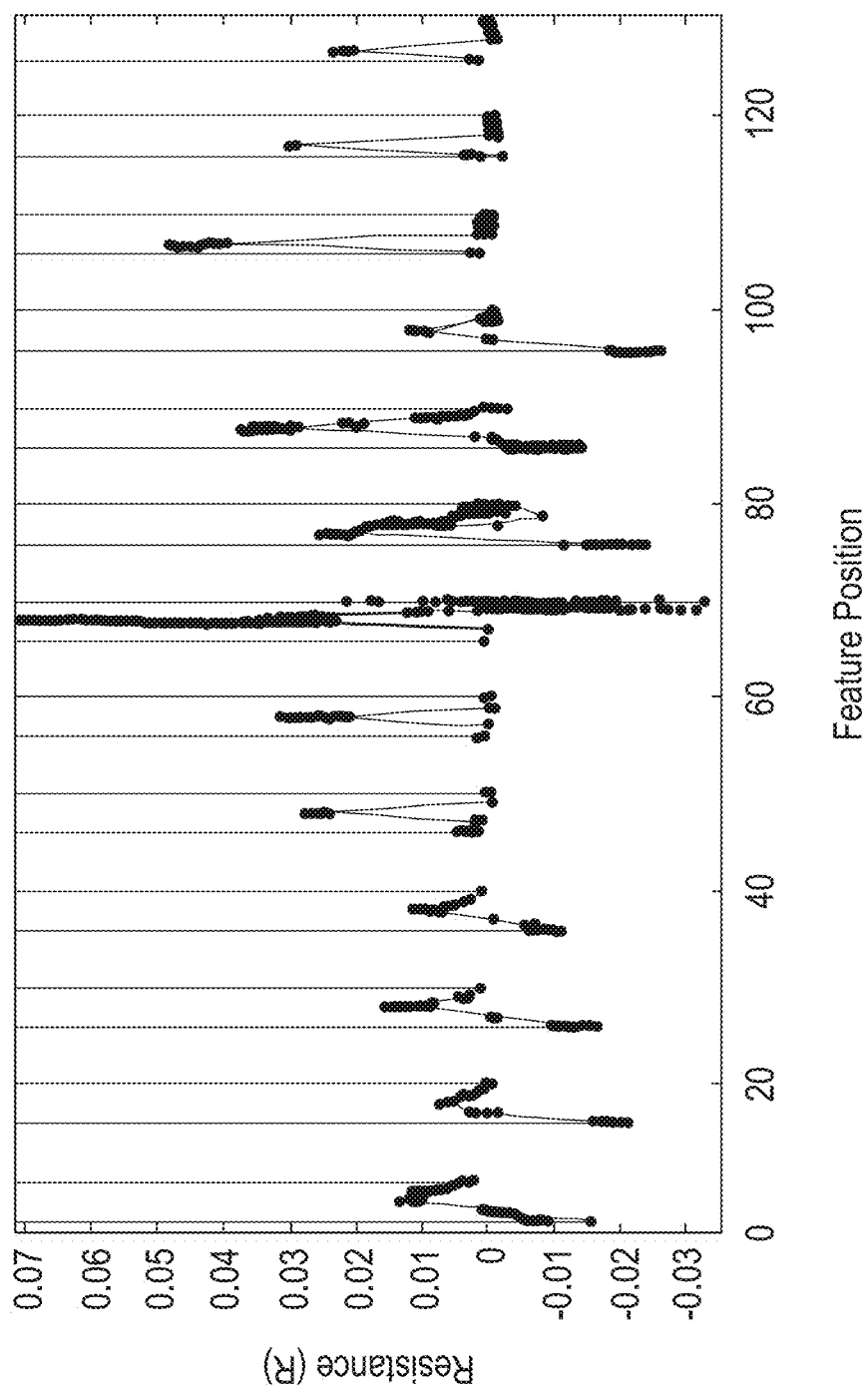
FIGS. 3A-3C are graphs showing the voltage drops for a biological (urine) sample using a slope feature extraction (FIGS. 3A and 3B) and mean-plus-slope feature extraction (FIG. 3C).
Figure 3B:
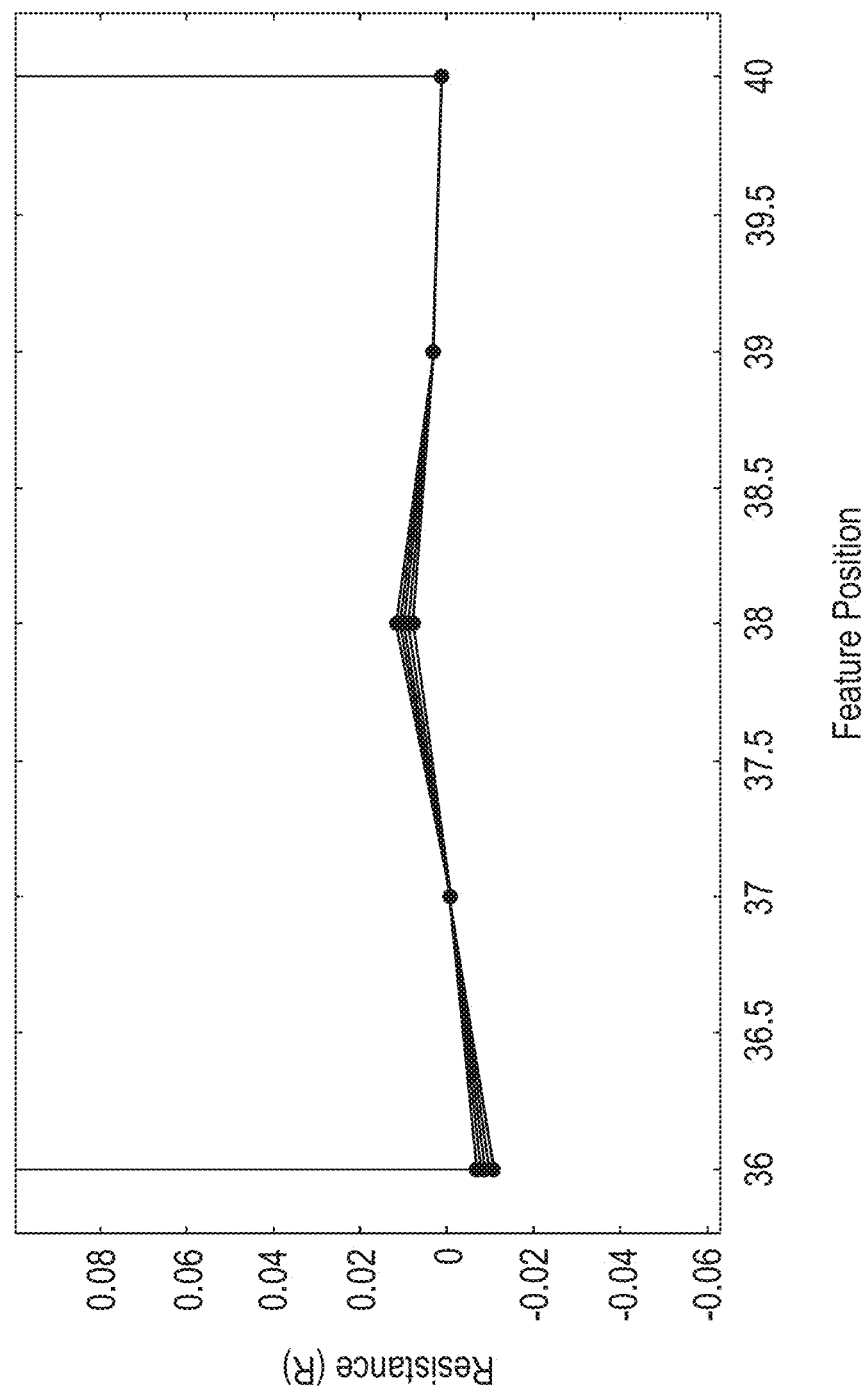
Figure 3C:
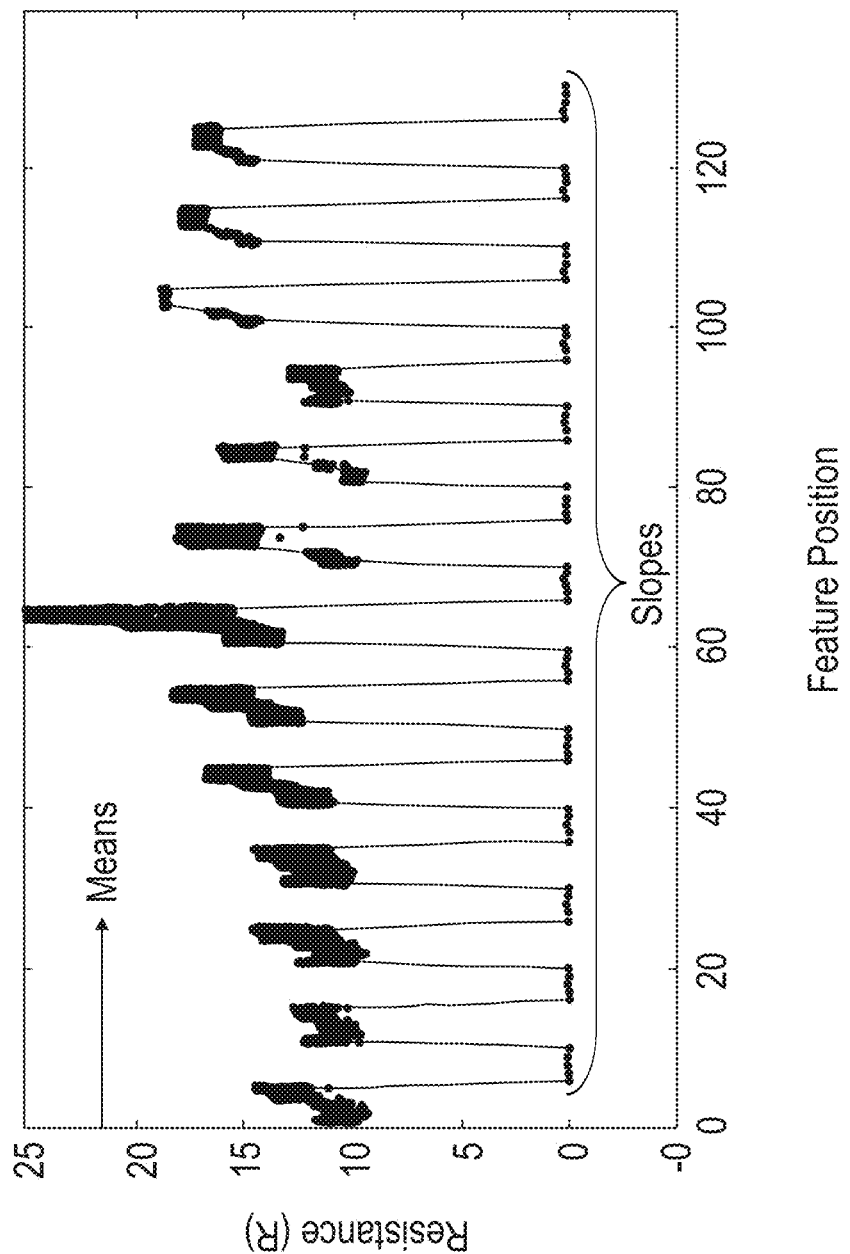

FIGS. 3A-3C show the voltage drops for a biological sample (i.e., normal human urine or NHU) using a slope feature extraction (FIGS. 3A and 3B) and a mean-plus-slope feature extraction (FIG. 3C). FIG. 3A, and more dramatically the zoomed perspective in FIG. 3B, show that the variations between different readings of the sample are not significantly distinguishable with a slope feature extraction. By contrast, when a mean-plus-slope feature extraction is applied to the sample, the different readings of the sample show pronounced variations. As is shown in FIG. 3C, the inclusion of low variation areas causes divergence of the classification algorithm.

Examples 2 and 3 describe the steps required to acquire training and test sets for an electronic nose used for a beverage application (Example 2) and for a biological application (Example 3). In Example 2, the following set of beverages were tested: orange juice, apple juice, lemonade, beer, and wine. In Example 3, two samples of NHU were separately inoculated with K12 *Escherichia coli* (*E. coli*) and uropathogenic *E. coli* (UPEC) to produce two separate urinary tract infection (UTI) samples, both of which were tested. The results of the NHU/UTI testing data set are shown in Table 1. As shown therein, all labels except for the K12 UTI sample were predicted with 100% accuracy (the K12 UTI sample was mislabeled as NHU on 17% of the tests). The results of Example 3 and Table 2 show that the gas sensing system described herein has high accuracy for detection of metabolomic VOCs and that electronic nose sensors built upon the platform described herein have the ability to identify and differentiate bacterial pathogens of the same genus from a single sample.

TABLE 1

| | | PREDICTED LABEL | | | |
|---|---|---|---|---|---|
| | | Air | NHU | K12 | UPEC |
| TRUE LABEL | Air | 1.00 | 0 | 0.0 | 0 |
| | NHU | 0 | 1.00 | 0 | 0 |
| | K12 | 0.0 | 0.17 | 0.83 | 0 |
| | UPEC | 0 | 0 | 0 | 1.00 |

Table 2 shows the results of application of the mean and the mean-plus-slope feature extraction methods described herein to classify a beverage from among the set of orange juice, apple juice, lemonade, beer, and wine (a beverage application) and a urine sample as either an NHU sample or a UTI sample (a biological application). For the biological application, mean feature extraction provided a significantly more accurate prediction than mean-plus-slope feature extraction. By contrast, for the beverage application, mean-plus-slope feature extraction provided a more accurate prediction of the beverage than mean feature extraction. The beverage application included two additional traditional extraction methods, LDA (linear discriminate analysis) and PCA+ANN (principal component analysis plus artificial neural network) for comparison purposes, both of which were found to not be statistically significant.

TABLE 2

| FEATURE EXTRACTION METHOD | BEVERAGE APPLICATION (Orange Juice Prediction Accuracy) | BIOLOGICAL APPLICATION (UTI Sample Prediction Accuracy) |
|---|---|---|
| MEAN | 67.96% | 97.91% |
| MEAN + SLOPE | 89.72% | 66.17% |
| LDA | 48.22% | |
| PCA + ANN | 52.65% | |

Figure 4A:
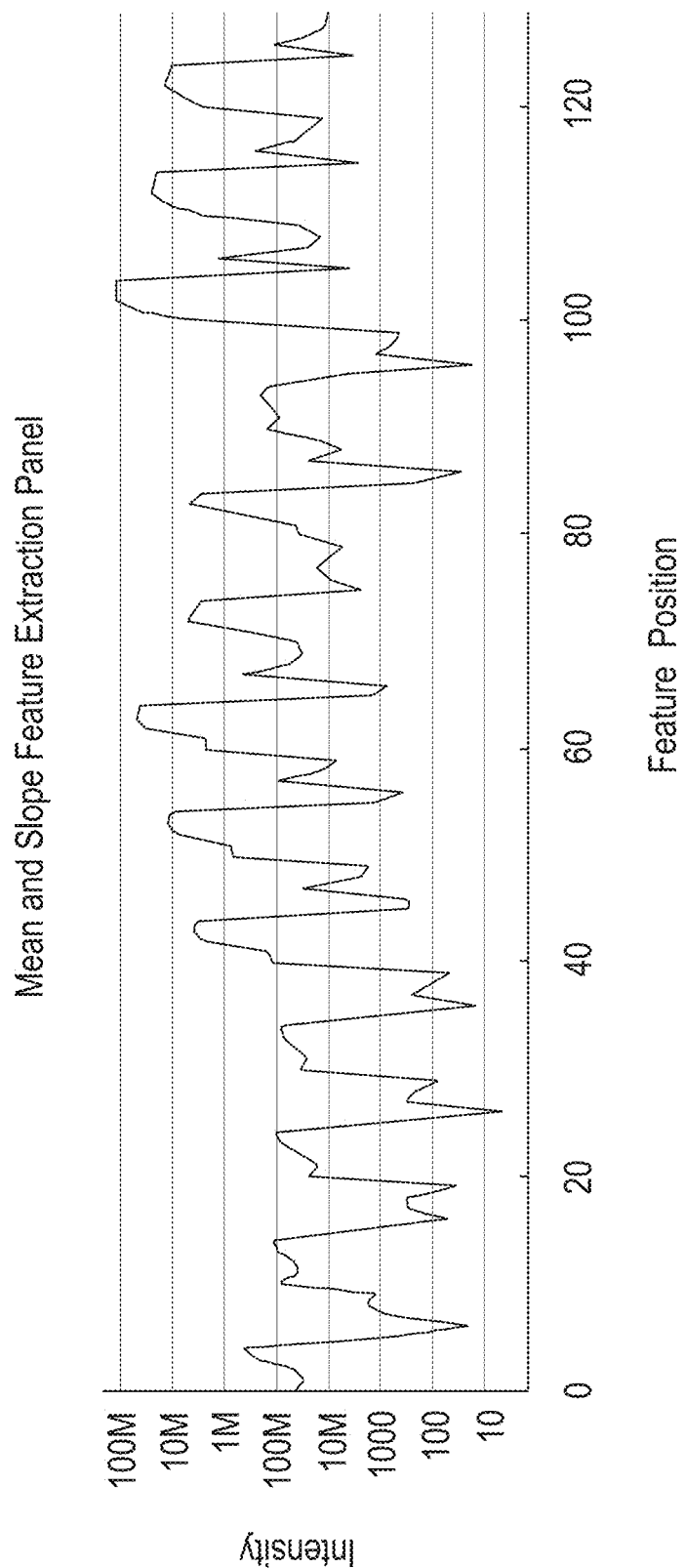
FIG. 4A and FIG. 4B show application of mean-plus-slope feature extraction on raw data from a beverage sample (FIG. 4A) and prediction of the beverage by feature extraction (FIG. 4B).
Figure 4B:
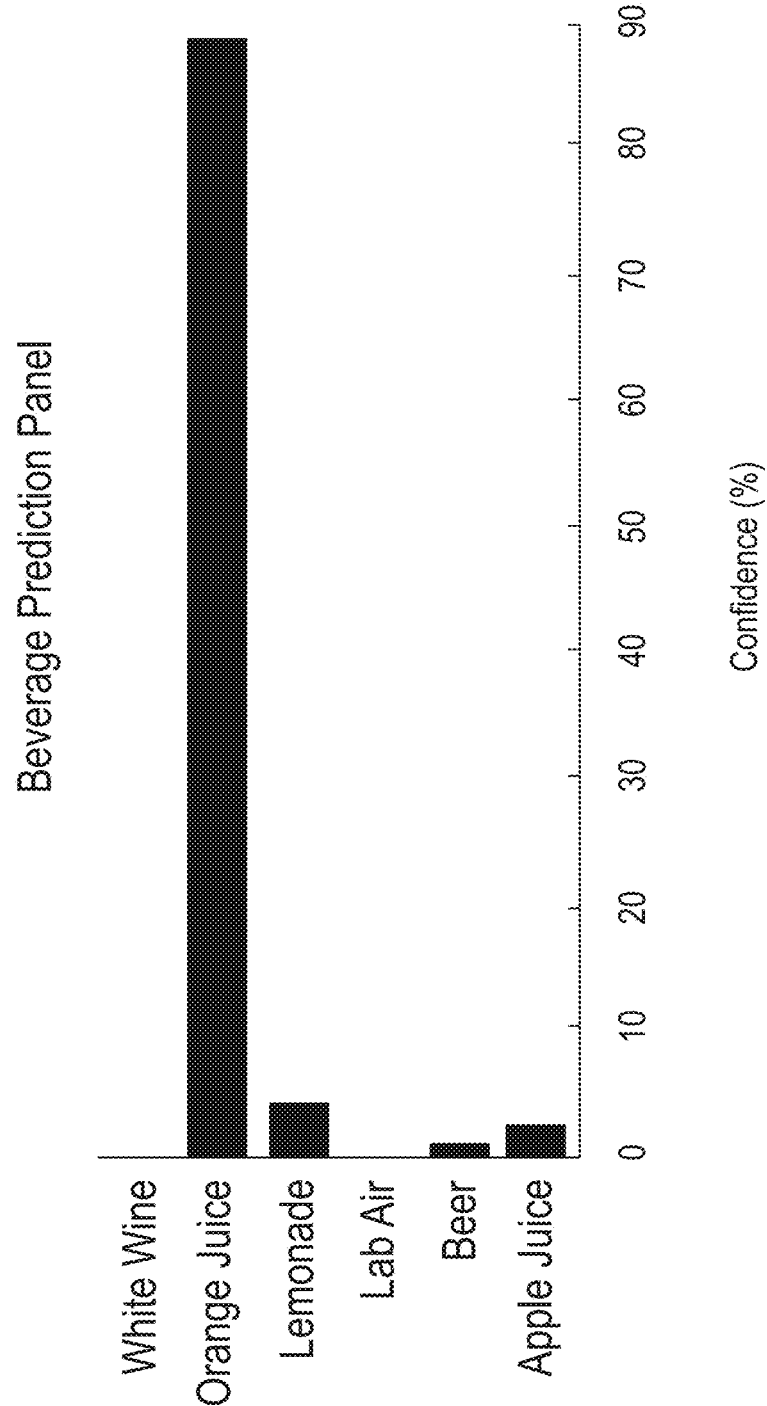

FIGS. 4A and 4B show the mean-plus-slope feature extraction panel (FIG. 4A) and the beverage prediction panel (FIG. 4B) for the beverage application of Table 2. As shown in Table 2 and FIG. 4B, the mean-plus-slope feature extraction of the tested beverage sample resulted in ~90% prediction accuracy for an orange juice beverage. FIG. 4B, further shows that the mean-plus-slope feature extraction produced no misclassification of the orange juice sample for lab air or wine and produced only negligible misclassification of the orange juice sample for lemonade, apple juice, and beer.

Figure 5A:
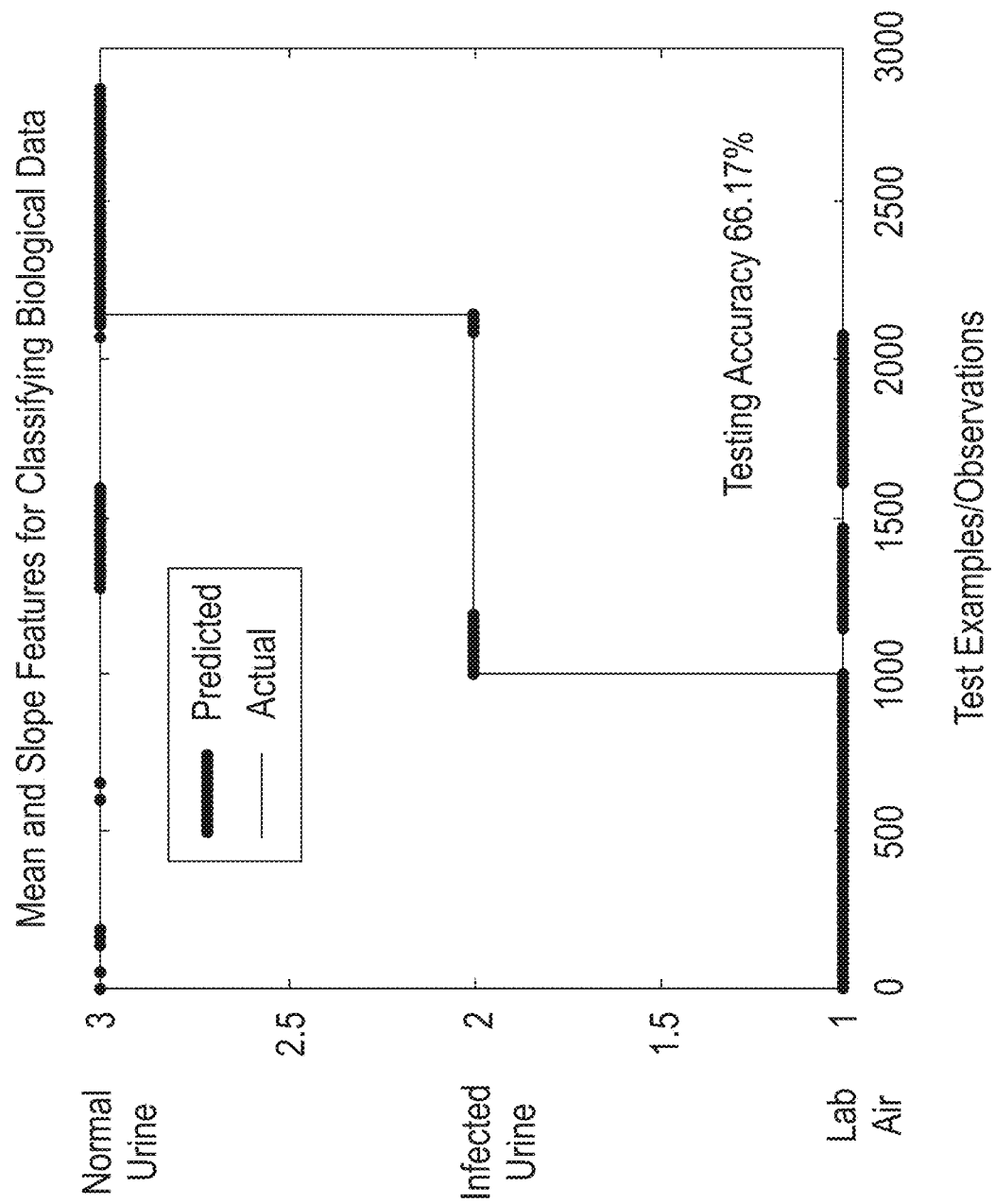
FIGS. 5A and 5B show the prediction results for the status of a biological (urine) sample that had its raw data processed with mean-plus-slope feature extraction (FIG. 5A) and mean feature extraction (FIG. 5B).
Figure 5B:
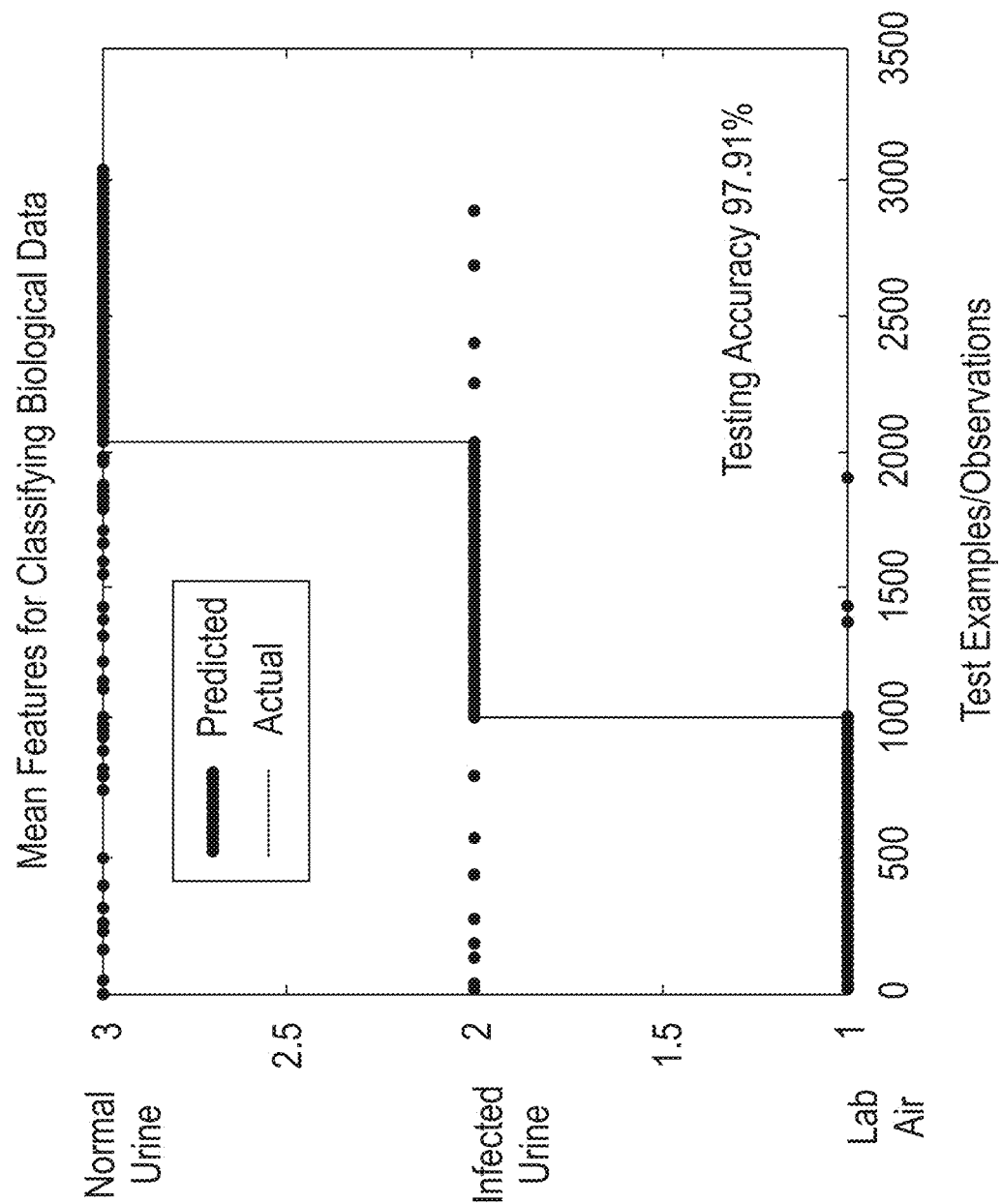

FIGS. 5A and 5B are graphs showing the prediction results for the biological application of Table 2. When mean-plus-slope feature extraction was applied to the urine test sample data, the accuracy of the predictions for NHU or a UTI was only 66.17% (FIG. 5A), but when mean feature extraction was applied to the same urine test sample data, the accuracy of the predictions for NHU or a UTI was 97.91% (FIG. 5B).

The results of Table 2 show that where samples are close in characteristics (e.g., biological samples, such as NHU and UTI samples), the mean feature extraction method is more reliable than the mean-plus-slope feature extraction method. By contrast, where samples are not close characteristically (e.g., a panel of sample beverages that includes orange juice, apple juice, lemonade, wine, and beer), the mean-plus-slope feature extraction method is more reliable than the mean feature extraction method.

Figure 6:
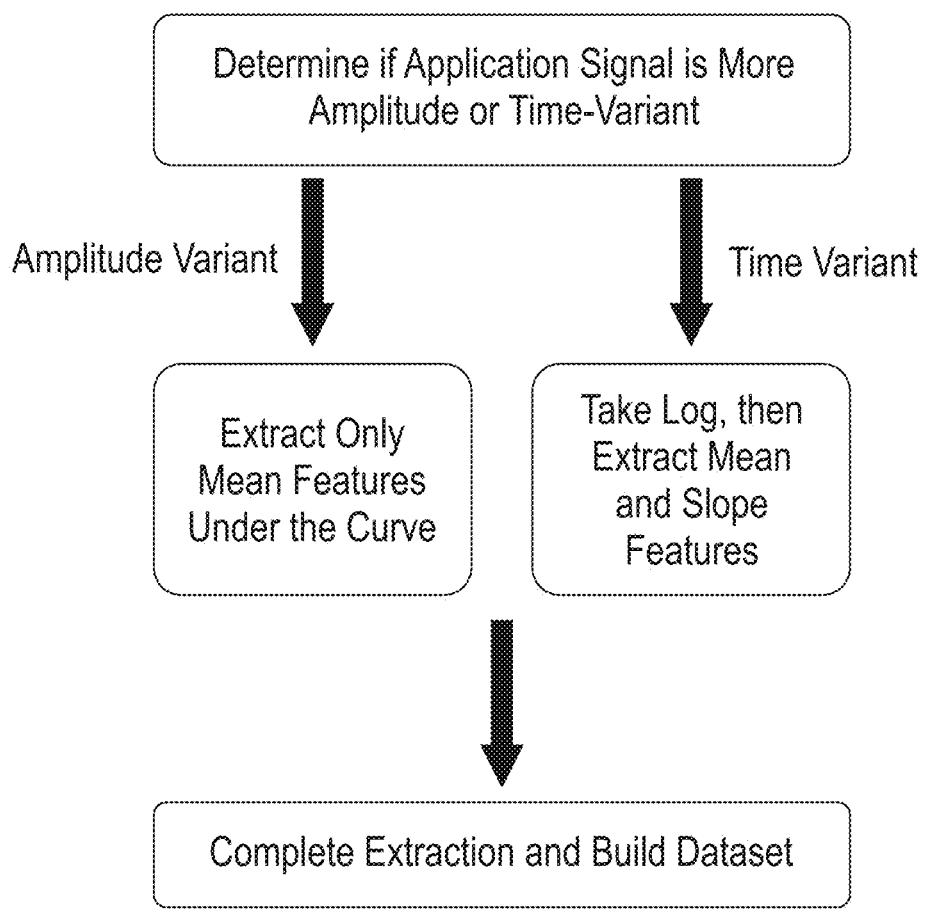
FIG. 6 is a schematic showing the steps for feature extraction selection for an electronic nose.

FIG. 6 is a schematic outlining feature extraction selection for an electronic nose. As shown therein, feature extraction selection for an electronic nose first involves determining if the application signal is primarily amplitude-variant or primarily time-variant. Target applications where the compounds of interest have similar functional groups and/or emit volatiles with similar chemical groups are usually amplitude-variant, while target applications where the compounds of interest have different functional groups and/or emit volatiles with different chemical groups are usually amplitude-and-time-variant. Examples of amplitude-variant target applications are biological and metabolomic tests, one example being the UTI tests described herein. Other amplitude-variant target applications are food and beverage tests, where the food and/or beverage belongs to a single class. For example, where the compounds of interest are two wine samples, the signals would be amplitude-variant because the two wine samples share an alcohol functional group. Similarly, beer and wine samples would also likely generate amplitude-variant output signals due to the shared alcohol functional groups of the two sample sets. By contrast, target applications that include non alcoholic and alcoholic compounds would be expected to produce amplitude-and-time-variant signals because the alcoholic and non-alcoholic samples would likely emit volatiles with different chemical groups.

Determining what type of feature to extract for a particular application requires visualizing the raw data signals from the application samples and identifying distinguishing factors such as sensitivity and amplitude variations between different samples, the sensor speed, and the shape of the signal variations. If samples are determined to be primarily amplitude-variant, mean features are extracted by chunking the raw data signals into slices and calculating the mean area under the curve, wherein values for all of the slices represent the curve for the amplitude-variant signals. If samples are determined to be primarily amplitude-and-time-variant, mean-plus-slope features are extracted by taking logarithmic values of the raw data signals and then calculating the mean area under the curve and the derivative of the curve, wherein all of the logarithmic values represent the curve for the amplitude-and-time variant signals. Taking the logarithm of the features diminishes the differences between samples; thus, if samples have close characteristics (i.e., are amplitude-variant), the logarithm of the feature may not be necessary or advisable. In some situations, the samples may not be dominant for either amplitude-variant or amplitude-and-time-variant signals; in such situations, both the mean and the mean-plus-slope features may need to be extracted. Once the extraction is complete, the datasets can be built in order to combine the extracted features into a format ready for machine learning.

The descriptions of the various embodiments of the present invention have been presented for purposes of illustration, but they are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

Example 1

Gas Sensor Set-Up

A set of six commercial metal oxide (MOX) gas sensors were individually mounted on a separate sensor module equipped with a printed circuit board (PCB) with an integrated microcontroller and the circuitry required to operate the sensor. The sensor module communicated via I2C protocol with a central hub (BEAGLEBONE® Black, BeagleBoard.org Foundation, Oakland Township, Mich., USA). A single-board computer orchestrated the sensor modules and processed the multisensorial output. Each of the six MOX sensors was operated using an individualized multi-step, periodic voltage profile applied to the heating element resulting in step wise changes in temperature of the device. The heater voltage was expressed as a percentage of the operating voltage recommended by the sensor manufacturer. The heater voltage profile period of each sensor was synchronized to 80 sec. The resistance of the MOX sensing element was monitored at a fixed voltage at a rate of 10 Hz. In addition, two commercial miniaturized environmental sensors (Bosch Model BME680, Bosch Sensortec GmbH, Reutlingen, Germany) were used to monitor the temperature, pressure, and relative humidity inside the sensor chamber and in the surrounding environment, at a rate of 0.1 Hz.

Example 2

Beverage Prediction from VOCs

Six MOX sensors were set up as described in Example 1 and placed in a sealed chamber.

Five beverage samples were prepared by pouring 5 mL of liquid into a 20 mL vial equipped with a membrane cap. The beverages used were: orange juice, apple juice, lemonade, beer, and wine. An additional empty 20 mL vial, also equipped with a membrane cap, was used as reference sample and for flushing the system with air drawn from the surrounding environment. The membrane caps on each vial were punctured twice to create an inlet and an outlet. A one-way valve was placed at the inlet to prevent exposure of the sample to the environment (when the vial was not in use) and a particle filter was also placed at the inlet to prevent accumulation of particulate in the vial. The five vials were connected to a computer-controlled selector element (VICI® multipurpose actuator mobile control unit, Valco Instruments Co., Inc., Houston, Tex., USA), which in turn was connected to the sealed chamber containing the six MOX sensors. The selector element was used to determine from which individual vial headspace the vapors were drawn. A vacuum pump (Parker Model B.1F15E1.A12 VDC, Parker Hannifin, Hollis, N.H., USA) was placed downstream to a sealed chamber containing the six MOX sensors. The vacuum pump was regulated to generate a flow of 150 sccm through the sensor chamber, selector element, and selected vial (one vial of the five was selected at a time). In operation, the vapors from the individual vials flowed from the vial headspace to the sensor chamber where the vapors interacted with the MOX sensor to trigger changes in the resistance of the sensors. The flow of the beverage sample vapors through the system was measured with a Mass Flow Meter (ALICAT WHISPER™, Model MW-2SLPM-D/5M, Alicat Scientific, Tucson, Ariz., USA).

Training and test data were acquired by connecting each vial, in turn, to the sensor chamber via the selector element for a duration of 10 minutes. In between the data acquisitions, the MOX sensors were flushed for five minutes to promote sensor recovery by connecting the empty 20 mL vial to the sensor chamber and allowing the air flow to remove the vapors of the previous sample. By means of the selector element, each vial was repeatedly selected in a cyclic fashion over the course of several hours of data acquisition, after which time the vials containing the beverage samples were disposed of and replaced with new beverage samples in fresh vials.

The output of each MOX sensor consisted of the following data: sensor module ID, timestamp, sensor resistance, and heater voltage. The sensor output data were recorded in real-time for the duration of the experiment and stored in a separate text file for each sample exposure. The raw data were processed according to the schematic of FIG. 1 to extract the feature set, which was input into the classification algorithms.

Example 3

Metabolomic Marker Prediction from VOCs

Six MOX sensors were set up as described in Example 1.

Two liquid UTI samples were cultured by inoculating NHU (UTAK Laboratories, Valencia, Calif., USA) with two separate *Escherichia coli* (*E. coli*) samples (Migula; Castellani and Chalmers; ATCC® 29425™ and ATCC® 700928™; ATCC, Manassas, Va., USA) with comparable cellular counts. Prior to inoculation, the NHU was centrifuged and filtered with 0.2 μm filters to remove sediments and to aid in homogeneity of samples. Each of the *E. coli* strains were separately inoculated into the NHU at a fixed concentration and incubated at 37° C. over five days to guarantee a terminal concentration of $10^9$ CFU/mL. After the samples were plated, they were further filtered to remove cellular bodies of the bacteria leaving only emitted metabolomic volatiles in the sample. The metabolomic volatiles were separated into two sample volumes of 5 mL in Wheaton septa top vials (DWK Life Sciences, Millville, N.J., USA) for measurement. The samples measured were filtered uropathogenic *E. coli* (UPEC) and K12 *E. coli* in NHU. Lab air as was used as a reference.

Collection of data for training and test sets were made at different times with a minimum of an eight-hour gap between collection times. The training dataset consisted of two experiments and the test dataset was a third sequential experiment. The training dataset consisted of 1592 sample readings and the test dataset consisted of 3000 sample readings. Training accuracy was 100%. Headspace measurements of each of the four sample vials were made using the six MOX sensors. The sequence of collection from the sample vials was randomized over the course of an eight-hour collection period with an air flush between vials. Samples were incubated at 27° C. during measurements to aid in the evaporation of trapped volatiles. The sensor response was saved using a Data Acquisition System (DAS) before feature extraction and labeling of the sensor data were performed. Machine learning with the small classifiers support vector machine (SVM), logistic regression, and random forest was performed to identify the odor classes from the testing dataset. The machine learning resulted in the data shown in Table 1.

We claim:
1. A method comprising the steps of:
(a) obtaining at least one compound of interest for testing on at least one gas sensor;
(b) obtaining multiple output signals from the at least one gas sensor for the at least one compound of interest;
(c) determining whether each of the multiple output signals is an amplitude-variant signal or an amplitude-and-time-variant signal; and
(d) for any amplitude-variant output signal, extracting its mean features, and for any amplitude-and-time-variant output signal, extracting its mean-plus-slope features, wherein,
mean feature extraction is performed on any amplitude-variant output signals by chunking each of the amplitude-variant output signals into slices and calculating mean area under the curve, wherein values for all of the slices represent the curve for the amplitude-variant signals, and
mean-plus-slope feature extraction is performed on any amplitude-and-time-variant output signals by taking logarithmic values for each of the amplitude-and-time-variant output signals and calculating mean area under the curve, wherein all of the logarithmic values represent the curve for the amplitude-and-time-variant output signals.

2. The method of claim 1, comprising:
(e) combining the extracted mean features and/or the extracted mean-plus-slope features to classify the at least one compound of interest.

3. The method of claim 1, wherein the at least one compound of interest is a volatile organic compound (VOC).

4. The method of claim 1, wherein the at least one compound of interest comprises at least two compounds of interest and the amplitude-variant output signals indicate that the at least two compounds of interest share similar functional groups and emit volatiles with similar chemical groups.

5. The method of claim 1, wherein at least one compound of interest is at least two compounds of interest and the amplitude-and-time-variant output signals indicate that the at least two compounds of interest have different functional groups and emit volatiles with different chemical groups.

6. The method of claim 1, wherein the at least one gas sensor is part of a gas sensor array.

7. The method of claim 1, wherein the extracted features are formatted for machine learning processing.

8. A method for fine-tuning features from raw data comprising:
(a) obtaining multiple output signals for at least one compound of interest;
(b) determining if the multiple output signals are amplitude-variant or amplitude and time-variant through visualization of the multiple output signals; and
(c) extracting features from the raw data for the multiple output signals,
wherein,
mean features are extracted on the raw data from the multiple output signals that are amplitude-variant by chunking the amplitude-variant raw data into slices and calculating mean area under the curve, wherein values for all of the slices represent the curve v, and
mean-plus-slope features are extracted on the raw data from the multiple output signals that are amplitude-and-time-variant by taking logarithmic values of the amplitude-and-time-variant raw data and calculating mean area under the curve, wherein all of the logarithmic values represent the curve for the amplitude-and-time-variant output signals.

9. The method of claim 8, wherein the multiple output signals are obtained from a gas sensor array.

10. The method of claim 8, wherein the at least one compound of interest is a volatile organic compound (VOC).

11. The method of claim 8, wherein the at least one compound of interest is at least two compounds of interest and the amplitude-variant output signals indicate that the at least two compounds of interest share similar functional groups and emit volatiles with similar chemical groups.

12. The method of claim 8, wherein the at least one compounds of interest is at least two compounds of interest and the amplitude-and-time-variant output signals indicate that the at least two compounds of interest have different functional groups and emit volatiles with different chemical groups.

13. The system of claim 12, wherein the at least one algorithm formats the extracted features for machine learning processing.

14. The system of claim 12, wherein the at least one compound of interest is a volatile organic compound (VOC).

15. The system of claim 12, wherein the at least one compound of interest is at least two compounds of interest and the amplitude-variant output signals indicate that the at least two compounds of interest share similar functional groups and emit volatiles with similar chemical groups.

16. The system of claim 12, wherein the at least one compound of interest is at least two compounds of interest and the amplitude-and-time-variant output signals indicate that the at least two compounds of interest have different functional groups and emit volatiles with different chemical groups.

17. The method of claim 8, wherein the extracted features are formatted for machine learning processing.

18. A system comprising:
a sensor array comprising a plurality of gas sensors for testing at least one compound of interest, wherein output signals from each sensor of the sensor array are amplitude-variant output signals and/or amplitude-and-time-variant output signals; and
a microprocessor comprising at least one algorithm in communication with the sensor array, wherein the microprocessor applies mean feature extraction on any amplitude-variant output signals and mean-plus-slope feature extraction on any amplitude-and-time-variant output signals.

19. The system of claim 18, wherein the microprocessor extracts mean features from the output signals by chunking values of the amplitude-variant output signals into slices and calculating mean area under the curve, wherein values for all of the slices represent the curve for the amplitude-variant output signals.

20. The system of claim 18, wherein the microprocessor extracts mean-plus-slope features from the output signals by taking logarithmic values of the output signal values and calculating mean area under the curve, wherein all of the logarithmic values represent the curve for the amplitude-and-time-variant output signals.

21. A system comprising:
a sensor array comprising a plurality of gas sensors for testing at least one compound of interest, wherein output signals from each sensor of the sensor array are amplitude-variant output signals; and
a microprocessor comprising at least one algorithm in communication with the sensor array, wherein the microprocessor applies mean feature extraction on the output signals by chunkin values of the amplitude-variant output signals into slices and calculating mean area under the curve, wherein values for all of the slices represent the curve.

22. The system of claim 21, wherein the at least one algorithm formats the extracted features for machine learning processing.

23. The system of claim 21, wherein the at least one compound of interest is a volatile organic compound (VOC).

24. The system of claim 21, wherein the at least one compounds of interest is at least two compounds of interest and the amplitude-variant output signals indicate that the at least two compounds of interest share similar functional groups and emit volatiles with similar chemical groups.

25. A system comprising:
a sensor array comprising a plurality of gas sensors for testing at least one compound of interest, wherein output signals from each sensor of the sensor array are amplitude-and-time-variant output signals; and
a microprocessor comprising at least one algorithm in communication with the sensor array, wherein the microprocessor applies mean-plus-slope feature extraction on the output signals.

26. The system of claim 25, wherein the microprocessor extracts mean-plus-slope features from the output signals by taking logarithmic values of the output signal values and calculating mean area under the curve, wherein all of the logarithmic values represent the curve.

27. The system of claim 25, wherein the at least one algorithm formats the extracted features for machine learning processing.

28. The system of claim 25, wherein the at least one compound of interest is a volatile organic compound (VOC).

29. The system of claim 25, wherein the at least one compounds of interest is at least two compounds of interest and the amplitude-and-time-variant output signals indicate that the at least two compounds of interest have different functional groups and emit volatiles with different chemical groups.

* * * * *